United States Patent

Nomura et al.

[11] Patent Number: 5,092,861
[45] Date of Patent: Mar. 3, 1992

[54] DISPOSABLE GARMENTS

[75] Inventors: Hironori Nomura, Iyomishima; Takamitsu Igaue, Kawanoe; Hiroki Yamamoto, Kawanoe; Hiroyuki Tanji, Kawanoe, all of Japan

[73] Assignee: Uni-Charm Corporation, Ehime, Japan

[21] Appl. No.: 632,992

[22] Filed: Dec. 24, 1990

[30] Foreign Application Priority Data

Dec. 22, 1989 [JP] Japan .................................. 1-333415

[51] Int. Cl.⁵ ............................................. A61F 13/15
[52] U.S. Cl. .................................. 604/385.2; 604/358
[58] Field of Search ...................... 604/385.2, 385, 391, 604/358

[56] References Cited

U.S. PATENT DOCUMENTS

| | | | |
|---|---|---|---|
| 4,050,462 | 9/1977 | Woon et al. | 604/385.2 |
| 4,795,451 | 1/1989 | Buckley | 604/385.2 |
| 4,816,026 | 3/1989 | Richardson | 604/385.2 |

Primary Examiner—Randy C. Shay
Assistant Examiner—G. Gualtieri
Attorney, Agent, or Firm—Fred Philpitt

[57] ABSTRACT

Here are disclosed disposable garments such as a diaper having adhesive areas on top- and/or backsheet(s) along leg-openings. Each of the adhesive areas is defined by a plurality of spiral adhesive traces. The stretchable elastic means are bonded to the top- and/or backsheet(s) along the adhesive areas, respectively.

4 Claims, 2 Drawing Sheets

DISPOSABLE GARMENTS

BACKGROUND OF THE INVENTION

The present invention relates to disposable garments and, more particularly, to garments such as diaper, incontinence pants or baby training pants.

Garments of such type are usually provided around respective leg-openings with elastic means. Conventionally, the elastic means under being stretched at a desired elongation percentage are bonded to at least one of the top- and backsheets with adhesive applied onto the elastic means themselves. The procedure has been also proposed according to which the elastic means under being stretched at a desired elongation percentage are bonded to the top- or backsheet with adhesive applied onto the top- or backsheet.

The top- and backsheets in such garments preferably have high stretchability and suppleness in view of function to be performed by the garments. However, both the garments of prior art as have been referred to utilize continuous application of hot melt type adhesive and, therefore, stretchability as well as suppleness of the top- and/or backsheet(s) are necessarily sacrificed particularly when adhesive must be applied onto the elastic means or at least one of top- and backsheets in consideration of number, width or diameter of the elastic means.

In conventional practice to fix the elastic means to the top- and/or backsheet(s) by curving the elastic means while being stretched in an arc so as to extend along the leg-opening and bonding them to the top- and/or backsheet(s), the elastic means tend to restore their initial rectilinear position under their contractability immediately after they have been bonded to the sheet(s) and sometimes they are fixed to the sheet(s) at the position offset transversely from the proper position of fixation with respect to their longitudinal direction.

Accordingly, it is an object of the present invention to provide disposable garments having around the top- and/or backsheet(s) around the leg-openings adhesive areas each defined by a plurality of spiral adhesive traces on which the elastic means are mounted so that stretchability as well as suppleness of the top- and/or backsheet(s) are not sacrificed and the elastic means once mounted on the adhesive areas are not displaced therefrom.

SUMMARY OF THE INVENTION

The object set forth above is achieved, according to the present invention, by disposable garments comprising a topsheet, a backsheet, and stretchable elastic means mounted around leg-openings formed on opposite sides of a crotch section defined between front and rear sections of the sheets, wherein there are provided adhesive areas on at least one of said top- and backsheets along curved configurations of the leg-openings, each of the adhesive area being defined by a plurality of looped adhesive segments, and the stretchable elastic means are bonded to at least one of the top- and backsheets along the adhesive areas, respectively.

Preferably, the stretchable elastic means are stretchable transversely of axes of the respective spiral adhesive traces defining the adhesive areas.

Preferably, each of the elastic means comprises first and second elastic members, respective intermediate portions of the first and second elastic members being positioned substantially at the central area of the crotch section, and opposite end portions of the first elastic member are positioned substantially along front halves of the leg-openings, respectively, while opposite end portions of the second elastic member are positioned substantially along rear halves of the leg-openings, respectively.

In the garments of the present invention constructed as have been described, each of the adhesive areas for fixation of the elastic means is defined by a plurality of looped adhesive segments having therein fine and many non-adhesive spaces. Such feature of the invention minimizes deterioration in stretchability and suppleness of the top- and backsheets due to presence of the adhesive areas even when the top- and backsheets comprise material having the stretchability and suppleness, such as fibrous non-woven fabric.

The feature that the adhesive areas are defined by groups of looped adhesive segments and preferably the elastic means are stretchable transversely of the axes of the respective looped adhesive segments is advantageous in that, even if the elastic means tend to restore their initial rectilinear positions, i.e., to contract transversely thereof (in the direction transverse of the adhesive areas) to their initial rectilinear positions immediately after the elastic means being stretched and curved so as to extend along the leg-openings have been bonded to the top- and/or backsheet(s) on the adhesive areas, this is prevented by the groups of looped adhesive segments. In addition, even if the elastic means have actually shifted by going beyond or breaking several looped adhesive segments, the elastic means are prevented from completely displacing from the associated adhesive areas transversely of the adhesive areas.

The elastic means comprise two elastic members adapted to diverge from each other so as to extend along front and rear halves of the respective leg-openings, respectively, and each elastic member comprises a plurality of filamentous elastic elements. Accordingly, a contracting force generated in one elastic member is not directly transferred to the other and thereby the shift or displacement can be avoided further effectively.

BRIEF DESCRIPTION OF THE DRAWINGS

A better understanding of the present invention can be derived by reading the ensuing specification in conjunction with the accompanying drawings wherein.

PREFERRED EMBODIMENT OF THE INVENTION

The present invention will be described with reference to an embodiment shown by the accompanying drawings.

Figure 1:
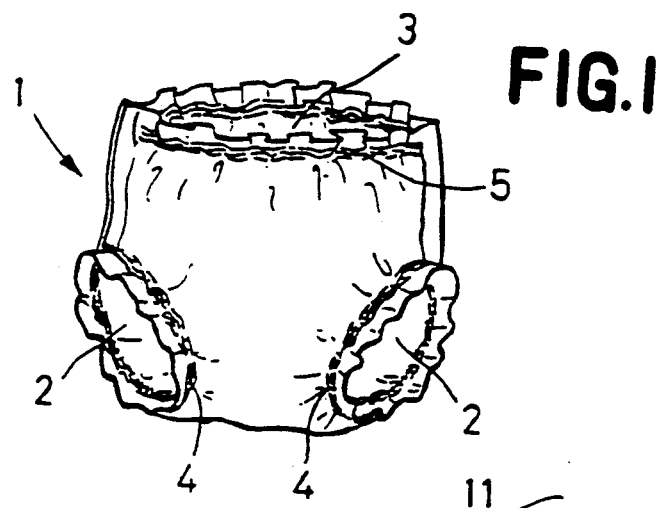
FIG. 1 is a perspective view, showing by way of example, garments of the present invention.

Referring to FIG. 1, garments 1 of the invention are illustrated in a perspective view. The garments 1 have leg-openings 2 and a waist (trunk) opening 3, and these openings are surrounded by associated elastic means 4, 5, respectively.

Figure 2:
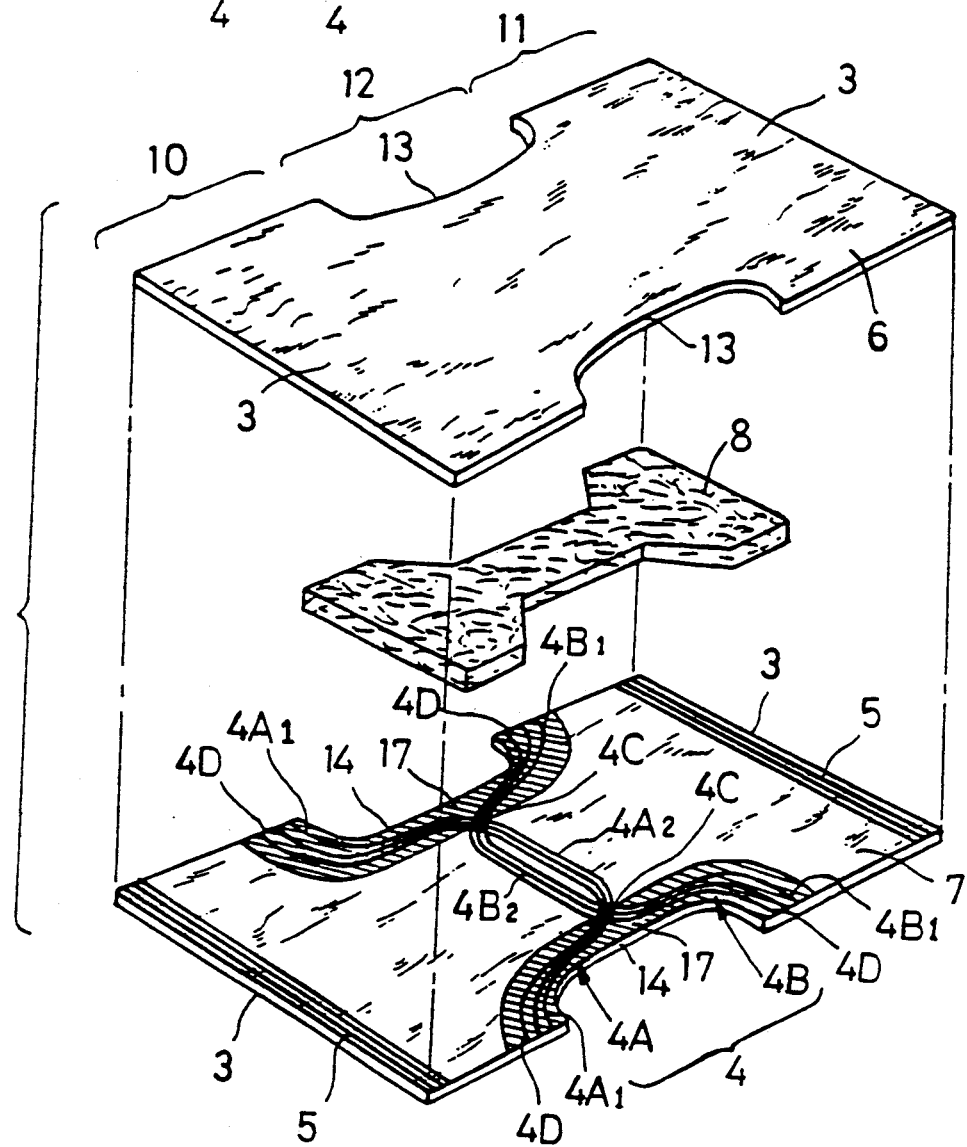
FIG. 2 is an exploded perspective view of the garments.

Referring to FIG. 2, the garments 1 are illustrated in an exploded perspective view. The garments 1 comprise a topsheet 6, a backsheet 7, a mat- or sheet-like core 8, and the elastic means 4, 5. A crotch section 12 interposed between front and rear sections 10, 11 of the top- and backsheets 6, 7 is formed along opposite side edges with notched edges 13, 14 which respectively define the leg-openings 2. The topsheet 6 comprises non-woven fabric being stretchable both in length and width and the backsheet 7 comprises non-woven fabric similar to the topsheet 6 and also being stretchable both in length and width. Though not shown, suitabe plastic film and the like stretchable both in length and width may be placed on and bonded to the inner side of the backsheet 7 with adhesive (including so-called hot melt type adhesive) intermittently applied onto one of the backsheet 7 and the plastic film and the like and, in addition, the plastic film and the like may be bonded also to the inner side of the topsheet 6 with adhesive intermittently applied onto one of the topsheet 6 and the plastic film and the like, if desired. In this manner, not only the stretchability of the top- and backsheets as the components of the garments 1 can be improved but also possible leakage of excretion liquid can be avoided.

The core 8 is sandwiched and bonded between the topsheet 6 and the backsheet 7 with adhesive applied intermittently applied onto one of these sheets. Intermittent application of adhesive is for the purpose and effect of maintaining the top- and backsheets 6, 7 stretchable and supple.

The top- and backsheets 6, 7 are provided in the crotch section 12 as well as in the front and rear sections 10, 11 with the leg-opening elastic means 4 and the waist-opening elastic means 5, respectively.

Each of the leg-opening elastic means 4 comprises a first elastic member 4A including a plurality of filamentous elastic elements and a second elastic member 4B including a plurality of filamentous elastic elements. These first and second elastic members 4A, 4B have their portions adjacent their opposite ends intersecting each other substantially at middle locations 4C along the respective notched edges 13, 14, respectively, so that respective portions $4A_1$, $4B_1$ of the first and second elastic members extending from the respective intersecting locations 4C to the outer ends 4D thereof are bonded to the inner side(s) of the top- and/or backsheet(s) along adhesive areas 17 which extend, in turn, along the respective notched edges 13, 14 while respective intermediate portions $4A_2$, $4B_2$ of the first and second elastic members are bonded neither to the sheets 6, 7 nor to the core 8 but positioned on the bottom side of the core 8 at a central area therof. The intermediate portions $4A_2$, $4B_2$ may be spaced from each other depending on various factors such as a size and a stiffness of the core 8. While the arrangement of the intermediate portions $4A_2$, $4B_2$ as in the illustrated embodiment is most preferred, these portions $4A_2$, $4B_2$ may be replaced by separate elastic elements and/or may be fixed to the backsheet 7. The elastic means 5 is bonded to the inner side of the top and/or backsheet(s) with adhesive around the waist-opening 3.

Figure 3:
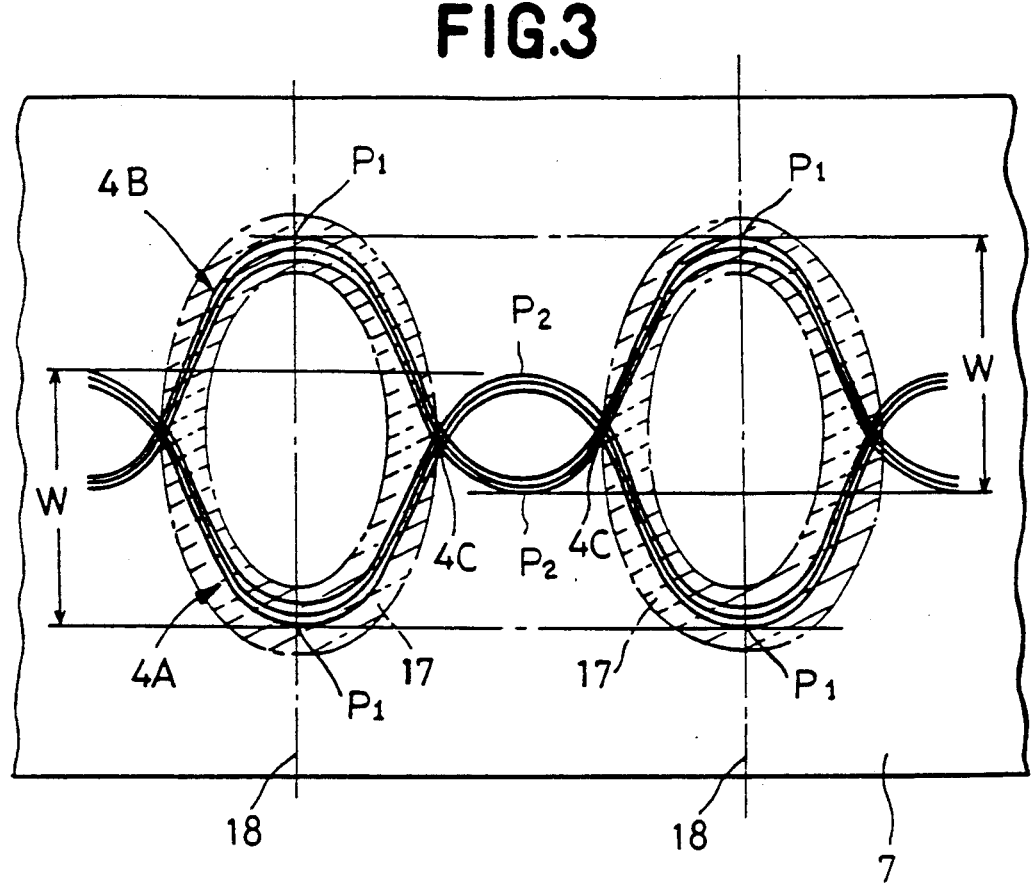
FIG. 3 is a plan view showing by way of example an arrangement of elastic means therein.

Now referring to FIG. 3, arrangement of the first and second elastic members 4A, 4B is illustrated by way of example in a plan view. During movement of the continuous backsheet 7 longitudinally thereof at a given velocity, adhesive is applied thereonto so as to surround individual ellipses successively arranged at given intervals to form adhesive areas 17 while the individual filamentous elastic elements of the first elastic member 4A and the second elastic member 4B are inserted into corresponding plural guide holes of first and second traverses (not shown) and the first and second traverses are actuated so that the first and second elastic members 4A, 4B are bonded to the backsheet 7 along the adhesive areas 17, describing curves substantially corresponding to sine curves each being symmetric with respect to the longitudinal centre line of the backsheet 7. The first and second elastic members 4A, 4B shift transversely of the backsheet 7 from a starting point $P_1$ to a turning point $P_2$ and from a turning point $P_2$ to a starting point $P_1$, respectively, by a width W. An elongation percentage and, therefore, an elongation stress increases as these elastic members 4A, 4B shift from the respective starting points $P_1$ to the respective turning points $P_2$, since the first and second elastic members 4A, 4B are stretched as the first and second elastic members 4A, 4B having been rectilinearly running longitudinally of the backsheet 7 while they are stretched at a given elongation percentage are now forcibly deflected transversely of the backsheet 7 by the respective traverses and a tension generated by such forcible deflection stretches the first and second elastic members 4A, 4B as they shift from the respective starting points $P_1$ to the respective turning points $P_2$. It should be noted here that the degree of such stretching effect depends on the velocity at which the first and second elastic members 4A, 4B rectilinearly run and the velocity at which the traverses transversely move. Spacings in the first and second elastic members 4A, 4B, each comprising a plurality of filamentous elastic elements, are reduced as these elastic members 4A, 4B are forcibly deflected by the associated traverses from running in parallel to the longitudinal direction of the backsheet 7 to the transverse direction, i.e., from the respective starting points $P_1$ to the respective turning points $P_2$. It should be noted again that a degree of such spacing reduction depends on the running velocities of the first and second elastic members 4A, 4B as well as of the backsheet 7. Portions (intermediate portions $4A_2$, $4B_2$, in FIG. 2) of the first and second elastic members 4A, 4B defined between each pair or adjacent intersections 4C slacken and get close to each other, because the backsheet 7 carries no adhesive on the area thereof facing these intermediate portions $4A_2$, $4B_2$. However, these intermediate portions $4A_2$, $4B_2$ also may be bonded to the backsheet 7 with adhesive.

On the continuous backsheet 7 thus provided with the first and second elastic members 4A, 4B, the cores 8 are placed at given positions, then the continuous topsheet 6 is placed on this assembly to form continuous laminate and this continuous laminate is severed along chain-lines 18 into individual laminates or garments. The individual laminate obtained in this manner is constructed as illustrated in an exploded perspective view by FIG. 2. In the individual laminate, opposite side portions $4A_1$, $4B_1$, of the first and second elastic members 4A, 4B, respectively, have their elongation stress gradually decreasing from their longitudinally inner ends (i.e., the respective intersections) 4C or adjacent the lower middle of each leg-opening toward their longitudinally outer ends 4D or the uppermost point of each leg-opening. In other words, the elongation stress gradually increases from their longitudinally outer ends 4D toward their longitudinally inner ends 4C. The spacings in the opposite side portions $4A_1$, $4B_1$ of the first and second elastic members 4A, 4B, respectively, are gradually enlarged from their longitudinally inner ends 4C (i.e., the respective intersections) toward their longitudinally outer ends 4D. In other words, the spacings are gradually reduced from their longitudinally outer ends 4D toward their longitudinally inner ends 4C.

Figure 4:
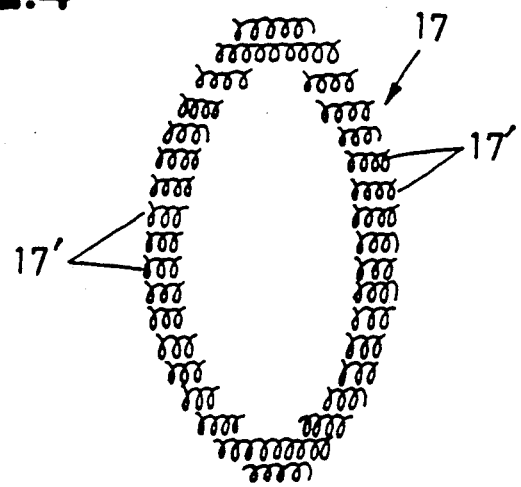
FIG. 4 is a plan view schematically showing a plurality of looped adhesive segments.

Referring to FIG. 4, each of the adhesive areas 17 is schematically illustrated in a plan view. The adhesive area 17 is defined by a plurality of looped adhesive segment 17'. These looped adhesive segments 17' have their axes oriented transversely of the backsheet 7 as viewed in FIG. 2, i.e., longitudinally of the continuous backsheet 7 as viewed in FIG. 3. Accordingly, the axes of substantially all the looped adhesive segments 17' extend transversely of the direction in which the first and second elastic members 4A, 4B extend. The first and second elastic members 4A, 4B are fixed to the backsheet 7 between, on or in the respective looped adhesive segments 17'. Therefore, even when the first and second elastic members 4A, 4B bonded to the backsheet 7 along the respective adhesive areas 17 so as to extend along the respective notched edges 13, 14 tend to restore their initial rectilinear positions, i.e., to restore their positions being transverse of the respective adhesive areas 17 under the effect of their contractibility, such restoration is prevented by the presence of the looped adhesive segments 17'. Even if the first and second elastic members 4A, 4B have shifted toward said direction by going beyond or breaking several looped adhesive segments 17', the elastic members will be prevented from complete displacing from the respective adhesive areas 17 toward said direction. The first and second elastic members 4A, 4B diverge from the respective intersections toward front and rear halves of the respective notched edges 13, 14 and, in addition, comprise the plural filamentous elastic elements, so that a direct transfer or contraction stress generated in one of these elastic members to the other elastic member never occurs and said shift or displacement is avoided further effectively. In the illustrated embodiment wherein each of the first and second elastic members 4A, 4B comprises a plurality of filamentous elastic elements, the previously mentioned function of the looped adhesive segments 17' expected with respect to the elastic members is more effective than in the case wherein each elastic member comprises an integral single member, because the elongation stress is distributed in a plurality of filamentous elastic elements and correspondingly weakened. Though not shown, the inner side of the topsheet 6 is also provided in conformity with the first and second elastic members 4A, 4B with adhesive areas similar to the adhesive areas 17.

The top- and backsheets 6, 7 are bonded together along their outer peripheral edges preferably by means of heat seal or adhesive. Preferably, the upper side of the core 8 also is intermittently bonded to the topsheet 6. Said individual laminate constructed in this manner is longitudinally folded in two and bonded along free opposite side edges by means of heat seal to form the garments 1 as shown by FIG. 1. Within the scope of the invention, it is also possible to provide opposite sides of the rear section with fasteners (not shown) to complete the waist-opening 3 as seen in the conventional disposable diaper of open type, instead of bonding the opposite free side edges of said individual laminate by means of heat seal. Accordingly, the present invention is not intended to be limited to the illustrated embodiment.

Non-woven fabric used as material for the top- and backsheets 6, 7 may be crimped fibrous web having weighing capacity and density enough to offer desired liquid-permeability while the core 8 may be an elastic molded mixture of fluffy pulp, other fibers and superabsorbent polymer particles.

It should be understood that the garments of the invention as have been described hereinabove may be manufactured, for example, by the method disclosed in Japanese Patent Application No. 1989-167224.

What is claimed is:

1. A disposable garment comprising a topsheet, a backsheet, and stretchable elastic means mounted around spaced apart leg-openings formed on opposite sides of a crotch section defined between front and rear sections of said sheets, spaced apart adhesive areas provided on at least one of said sheets along curved configurations of the leg-openings, each of said spaced apart adhesive areas being composed of a plurality of separated elongated segments of adhesive each segment having a longitudinal axis, each segment consisting of a plurality of connected loops arranged along the longitudinal axis of the segment and portions of said stretchable elastic means are bonded to at least one of said sheets by said spaced apart adhesive areas.

2. A garment as recited in claim 1 wherein substantially all of said stretchable elastic means are stretchable transversely of the longitudinal axes of said adhesive segments.

3. A garment as recited in claim 1 wherein each of said elastic means comprises first and second elastic members, intermediate portions of the first and second elastic members being positioned substantially in a central portion of the crotch section, and opposite end portions of said first elastic member are positioned substantially along front halves of the leg-openings, while opposite end portions of said second elastic member are positioned substantially along rear halves of the leg-openings.

4. A garment according to claim 1 wherein said adhesive areas are in the form of spaced apart halves of ellipses and said elastic means are arranged in configurations generally resembling intersection sine waves that are 180° out of phase with each other.

* * * * *